United States Patent
Lindström (10) Patent No.: US 10,987,256 B2
(45) Date of Patent: Apr. 27, 2021

(54) ABSORBENT ARTICLE IN THE FORM OF PANTS, SUCH AS NAPPY PANTS, SANITARY PANTS OR INCONTINENCE PANTS

(71) Applicant: SCA Hygiene Products AB, Gothenburg (SE)

(72) Inventor: Åsa Lindström, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 395 days.

(21) Appl. No.: 15/572,299

(22) PCT Filed: May 11, 2015

(86) PCT No.: PCT/SE2015/050523
§ 371 (c)(1),
(2) Date: Nov. 7, 2017

(87) PCT Pub. No.: WO2016/182484
PCT Pub. Date: Nov. 17, 2016

(65) Prior Publication Data
US 2018/0147098 A1 May 31, 2018

(51) Int. Cl.
*A61F 13/49* (2006.01)
*A61F 13/514* (2006.01)
(Continued)

(52) U.S. Cl.
CPC .... *A61F 13/51496* (2013.01); *A61F 13/4902* (2013.01); *A61F 13/496* (2013.01);
(Continued)

(58) Field of Classification Search
CPC ............ A61F 13/4906; A61F 13/49061; A61F 13/49019; A61F 13/4902; A61F 13/51394;
(Continued)

(56) References Cited

U.S. PATENT DOCUMENTS 6,297,420 B1  10/2001  Heincke
8,491,554 B2   7/2013  Carlucci et al.
(Continued)

FOREIGN PATENT DOCUMENTS

CN   1420751 A   5/2003
CN    143053 A   9/2003
(Continued)

OTHER PUBLICATIONS

Notice of Reasons for Rejection issued in Japanese patent application No. 2017-559009, dated Nov. 12, 2018 (3 pages) and its English-language translation thereof (3 pages).
(Continued)

*Primary Examiner* — Catherine L Anderson
(74) *Attorney, Agent, or Firm* — Buchanan Ingersoll & Rooney PC (57) ABSTRACT

An absorbent article in the form of pants includes: an absorbent core having two longitudinal edges and two transverse edges, and a pant part. The pant part includes a covering layer, a front section, a back section and an intermediate crotch section, wherein the front and back sections are connected to one another along two opposing longitudinal lateral edges to form a waist opening and a pair of leg openings. The absorbent core is arranged at least in the crotch section and connected to the covering layer on the side of the covering layer that is intended to face the wearer. The pant part includes at least one low-opacity area, which has an opacity that is lower than 50%. The article also includes a liquid-tight coloured barrier layer placed between said absorbent core and covering layer.

12 Claims, 3 Drawing Sheets

(51) Int. Cl.
*A61F 13/84* (2006.01)
*A61F 13/496* (2006.01)

(52) U.S. Cl.
CPC ........ *A61F 13/49019* (2013.01); *A61F 13/84* (2013.01); *A61F 2013/49025* (2013.01); *A61F 2013/49093* (2013.01)

(58) Field of Classification Search
CPC ...... A61F 13/51496; A61F 2013/15243; A61F 2013/49025; A61F 2013/49093; A61F 2013/51377; A61F 2013/8497
See application file for complete search history.

(56) References Cited

U.S. PATENT DOCUMENTS

| | | |
|---|---|---|
| 9,161,867 B2 | 10/2015 | Kawakami et al. |
| 9,737,441 B2 | 8/2017 | Song et al. |
| 2003/0114810 A1 | 6/2003 | Weber |
| 2006/0025737 A1 | 2/2006 | Song et al. |
| 2007/0032768 A1* | 2/2007 | Cohen ............... A61F 13/51496 604/385.01 |
| 2009/0306616 A1* | 12/2009 | Wennerback ..... A61F 13/15203 604/367 |
| 2013/0165890 A1 | 6/2013 | Glaug et al. |

FOREIGN PATENT DOCUMENTS

| | | |
|---|---|---|
| CN | 101022772 A | 8/2007 |
| CN | 104302259 A | 1/2015 |
| EP | 1 108 406 A2 | 6/2001 |
| EP | 1138293 A1 | 10/2001 |
| EP | 2554146 A1 | 2/2013 |
| EP | 2851046 A1 | 3/2015 |
| FI | 100453 B | 12/1997 |
| JP | 2003-285890 A | 10/2003 |
| JP | 2007-50145 A | 3/2007 |
| JP | 2007-312927 A | 12/2007 |
| JP | 2008-507386 A | 3/2008 |
| JP | 2013-255777 A | 12/2013 |
| WO | WO-02/07662 A1 | 1/2002 |
| WO | WO-2005/014085 A1 | 2/2005 |
| WO | WO-2006/038837 A1 | 4/2006 |

OTHER PUBLICATIONS

Extended European search report dated Mar. 1, 2019 issued in European patent application No. 15891989.4.
Written Opinion and Search Report dated Apr. 3, 2020 issued in Brazilian patent application No. BR112017023375-4.
First Chinese Office Action issued in Chinese patent application No. 201580079888.5, dated Jun. 10, 2020 (6 pages) and its English-language translation thereof (5 pages).

* cited by examiner (Prior art) Fig. 1

Fig. 5

ABSORBENT ARTICLE IN THE FORM OF PANTS, SUCH AS NAPPY PANTS, SANITARY PANTS OR INCONTINENCE PANTS

CROSS-REFERENCE TO PRIOR APPLICATION

This application is a § 371 National Stage Application of PCT International Application No. PCT/SE2015/050523 filed May 11, 2015, which is incorporated herein in its entirety.

TECHNICAL FIELD

An absorbent article in the form of pants, such as nappy pants, sanitary pants or incontinence pants including an absorbent core having two longitudinal edges and two transverse edges, a pant part, wherein said pant part includes a covering layer, a front section, a back section and an intermediate crotch section, wherein the front and back sections are connected to one another along two opposing longitudinal lateral edges in order to form a waist opening and a pair of leg openings, said absorbent core is arranged at least in the crotch section and connected to the covering layer on the side of the covering layer that is intended to face the wearer, said pant part includes at least one low-opacity area, which has an opacity that is lower than 50%, furthermore the article includes a liquid-proof, coloured barrier layer placed between said absorbent core and covering layer.

BACKGROUND

It is important that wearers of nappy pants, sanitary pants and/or incontinence pants feel that the article they wear is discreet in such a way that people in the wearer's vicinity do not see that he or she is using the absorbent protection. By using thinner and more flexible material for the pant material, it has been possible to increase the fit, flexibility and comfort of the article. In line with the fact that the pant material is thinner, its opacity will be less and the wearer's skin can thereby be seen through the pant material.

To meet the wearer's need for comfort but with retained security, the absorbent core that forms part of the article has been designed for a predetermined absorption requirement and placed mainly in the crotch area, in the area which is intended to receive the fluid that leaves the wearer's body.

By restricting the absorption part to the crotch area, the article will thus be experienced as less baggy.

A disadvantage when using an article in the form of pants, the pant material of which includes a thin material with low opacity in combination with an absorbent core and a barrier layer that only constitutes a part of the pants, is that the absorbent core and/or barrier layer appear very clearly through the pant material. The article is experienced as less discreet and of a nappy-like appearance due to the fact that the absorbent core and/or barrier layer are visible through the pants and not as the discreet underwear-like product that many wearers demand.

When wearing an article in the form of pants, the pant material of which includes a thin material with low opacity in combination with an absorbent core and a barrier layer that only constitutes a part of the pants, is that the absorbent core and/or barrier layer appear more or less clearly depending on the colour of the wearer's skin. The darker the skin tone, the more clearly the absorbent core and/or barrier layer, which seen traditionally is beige or white in colour, appear through the pant material of the article.

The prior art in the field is JP 200750145, which describes pants for use with light incontinence, the liquid-proof backing layer that forms a part of which is coloured or coated with the same colour as the outer layer, in order that the thickness of the absorption body shall be more discreet or similar to skin colour.

Document JP2007312927 describes nappy pants that include an inner layer consisting of at least one inelastic nonwoven layer and a beige outer layer consisting of an elastic nonwoven layer consisting of polyurethane elastomer.

It was previously known to design an article in the form of pants with a graphic pattern and colour in order to resemble conventional textile briefs as closely as possible. To meet this requirement, the pants have been designed with a typically conventional pattern in colour, for example longitudinal stripes in grey, blue or brown to resemble men's briefs, or a more feminine pattern, such as flowers, butterflies and/or colours that are regarded as being more associated with women.

A need thus remains to improve the discreetness of articles in the form of nappy pants.

SUMMARY

It is desired to achieve an article that has an underwear-like appearance with improved discretion, regardless of the wearer's skin tone.

Examples of embodiments of the invention are described here below.

The article is in the form of pants, such as nappy pants, sanitary pants or incontinence pants. The article is not limited to use by adults for the absorption of various bodily secretions, but can also be intended for use by young people, or by infants. The article can also be intended as a sanitary protection in the form of pants for the absorption of menstrual fluid.

By providing the article with a barrier layer with a skin-like colour, the article can be better adapted to a wearer with a specific skin tone and the article is improved by this during wearing. The wearer's skin can be seen through the article in the low-opacity area/areas outside the extension of the barrier layer. The skin-coloured barrier layer effectively conceals the intermediate core and shines through the low-opacity pant part and gives rise to the creation of an illusion for the people in the wearer's vicinity to believe that it is skin that is visible through the article, even in the area of the core/barrier layer.

An article executed according to embodiments of the invention is distinguished primarily by the fact that the difference between two colours in the colour space CIE L*a*b*, which is characterised by a Delta E-value (ΔE*ab) in a comparison between the low-opacity area/areas of the pant part above and outside the area of the barrier layer's extension, is less than 5 when said low-opacity area for the pant part has an opacity of 40-50%

4 when said low-opacity area for the pant part has an opacity of 30-40%

3 when said low-opacity area for the pant part has an opacity of 20-30%

2 when said low-opacity area for the pant part has an opacity of 0-20% when a reference surface with a predetermined skin-like colour is placed under the low-opacity area of the pant part, according to the test method described below.

A pant part having an opacity, for example, of 40-50% is more forgiving and permits a difference in the ΔE value that is greater compared with when the pant part has an opacity of around 20%.

As used herein, the "opacity" of a material means the characteristic ability of the material layer to visually conceal an underlying object or graphic pattern. Opacity is measured in percent, where 100% opacity means that nothing can be seen through the layer and 0% means that the material is completely transparent. The opacity is measured according to the method described here below.

As used herein, "low opacity" means that the material that constitutes the pant part has an opacity that is lower than 50%. Thus the material constituting the pant part does not have the characteristic ability to visually conceal an underlying object or graphic pattern.

According to one embodiment, the entire pant part can have an opacity lower than 50%, alternatively only certain areas have an opacity lower than 50%. If the pant part does not have an opacity lower than 50% over its entire extension, the part of the pant part that has an opacity lower than 50% extends at least partly over the extension of the barrier layer and further over any adjacent area or other area in the extension of the pant part.

The pant part can include a single layer, which can have a homogeneous structure with the same measured opacity over its entire plane or have a non-homogeneous structure and in this case with different opacity properties in different areas. An example of a pant part including a material with a non-homogeneous structure and with different opacity can include, for example, a woven material in which the material is more or less loosely woven, or be constituted of for example of a perforated lace-like material. The pant part can also include a material composed of different sizes and quality, which means that the pant part can acquire different opacity in different areas. One example is that the pant part includes a single inelastic nonwoven material with an opacity lower than 50%, which has also been provided with an elastic cuff-like material in the waist area in order to resemble traditional underpants more. The cuff-like material can have an opacity that differs from other areas of the pant part, have a different width from constituting only a narrow trim at the waist opening to extending far down towards the crotch section in the front and back sections respectively. Another example is that the pant part has an opacity lower than 50% on the whole and that the area for leg openings is provided with an elastic cuff-like material that has an opacity that differs from other areas of the pant part. A further example is that the pant part front and back sections are provided with an elastic material with an opacity lower than 50% in the areas where the front and back sections are connected to one another along two opposing longitudinal lateral edges to form an article with elastic side panels. The pant part is otherwise formed of a material that has an opacity that is lower than 50%.

Another way of achieving different opacity in different areas of the extension of the pant part is to provide an area having low opacity with a covering colour.

The area with low opacity can include a plurality of areas composed of different degrees of opacity, where certain areas have high opacity and certain areas have low opacity, which gives an average opacity that, is lower than 50%.

As used herein, the term "reference surface" refers to the surface that the pant part of the article is placed over in the actual measurement of the colour difference between the absorbent product in the area of the extension of the barrier layer and of said area of the pant part that has an opacity that is lower than 50%.

As used herein, the term "predetermined colour" for the reference surface means a number of predetermined colours precisely specified according to the CIE L*a*b* standard method on the reference surfaces that are included in the laboratory measurements of the article. These reference surfaces mirror colours of conceivable skin tones represented in the world, such as beige, yellow/red and dark brown. When selecting the colour of the respective reference surface that mirrors a conceivable skin tone, a selection was made from a colour chart "PANTONE SkinTone™ Guide-STG-201" purchased from Pantone LLC, World Headquarters, 590 Commerce Blvd. Carlstadt, N.J. 07072-3098. U.S.A. Pantone LLC is a company certified as complying with ISO 9001:2008. Colour samples forming part of the chart includes sheets of paper that have been coated with the respective colour. 110 different colour shades are included in the colour chart.

Three colours for the respective reference surface were selected from the "PANTONE SkinTone™ Guide-STG-201" colour chart to represent different conceivable skin tones and thus also to be able to describe the embodiments below in greater detail. These colours will be termed reference skin tone in the description.

"Light skin tone" is represented by the reference skin tone 5Y04 that has the following L*, a*, b* value; L*=67.9 a*=5.5 and b*=16.4.

"Yellow/red skin tone" is represented by the reference skin tone 4Y10 and has the following L*, a*, b* value; L*=52.6 a*=7.0 and b*=20.3.

"Dark skin tone" is represented by the reference skin tone 2R15 and has the following L*, a*, b* value; L*=30.1 a*=5.8 and b*=4.5.

The colour is measured according to a standard procedure from CIE (Commission Internationale de l'Eclairage), defined in 1976. The colour space is divided into three axes. L* represents lightness and the axis extends from 0 (black) to 100 (white). The axis a* goes from green to red, where positive values indicate more saturated red, and negative values more saturated green. The b* axis goes from blue to yellow, where positive values represent more saturated yellow and negative values more saturated blue. This colour space is well known in industry and is generally referred to as CIE L*a*b* or CIELAB (1976). Measurements are carried out using a spectrophotometer. An example of a suitable apparatus is the "Spectrophotometer CM-5" from Minolta (Japan), with accompanying manual. Light source D65 is used, and the observation angle 10°. The instrument is set to "SCE" (Specular Component Excluded).

A difference between two colours in the colour space CIE L*a*b* is characterised by a Delta E-value (ΔE*ab). The differences between the colours on the three respective axes are squared in this, following which the differences are summed and the root derived from the sum: $\Delta E^*ab = ((\Delta L^*)^2 + (\Delta a^*)^2 + (\Delta b^*)^2)^{0.5}$.

According to one embodiment, the extension of the barrier layer coincides on the whole with the extension of the absorbent core. The advantage in limiting the barrier layer to the main extension of the core is to increase the comfort for the wearer. The barrier layer can include a liquid-tight plastic film, a hydrophobic nonwoven layer or a nonwoven layer that has been treated to acquire liquid-inhibiting properties, or any other flexible material layer that has the capacity to resist liquid penetration. However, it can be advantageous if the barrier layer has a certain breathability, i.e. permits the passage of water vapour through the layer. The barrier layer can also include several materials that have been joined together to form a composite laminate. The layers can advantageously be connected by adhesive or any mechanical processing suitable for the materials involved. Examples of a mechanical joining method can be ultrasonic joining or joining via pressure and heat.

By limiting the barrier layer to mainly the core's extension, cost savings can be made and in addition the wearer's comfort is increased. Even if the barrier layer should include a breathable layer, the absorbent article would be experienced as warmer if the barrier layer constituted not only the area of the absorbent core but also the rest of the pants, since each added material increases the occlusion of the wearer's skin.

The measured colour/colour shade of the individual barrier layer, the colour/colour shade that was measured for the barrier layer without the influence of the covering layer, has an L* value of 30.1-67.9, an a* value of 5.5-7.0 and a b* value of 7.5-20.3.

The absorbent core can be constructed from absorbent material such as cellulose fluff pulp, wet laid paper, absorbent foam etc. It is also usual for the core to contain superabsorbents, i.e. polymer materials that can absorb bodily fluid corresponding to several times their own weight, forming a hydrogel. Such superabsorbents are normally present in the form of particles, but also fibres, flakes, granulate, foam and film occur. Furthermore, the absorbent core can include non-absorbent components such as stiffening elements, moulding elements, binding agents etc. Different types of liquid-receiving and liquid-distributing structures such as fibre pads, open-cell foam, dispersion layers or the like can also form part of the absorbent core. The core can thus include one or more layers stacked on top of one another. The design of the core for the optimum receiving and distribution of liquid in the structure also commonly occurs, for example recesses or liquid-dispersing channels. The design of the absorbent core can thus be adapted to the quantity of liquid that the core is expected to absorb. The type of bodily secretions to be absorbed and the manner in which the bodily secretions are to be emitted to the absorbent core are naturally also significant for the size and nature of the core.

According to another embodiment, the pant part has at least in part an opacity lower than 50% in the area of the extension of the barrier layer and further outside the edges of the core, which area adjoins the longitudinal edges of the core.

According to another embodiment, the pant part has at least in part an opacity lower than 50% in the area of the extension of the barrier layer and further outside the edges of the core, which area adjoins around the extension of the core.

According to yet another embodiment, the pant part includes a covering layer, which includes an elastic web material. The covering layer constitutes the front and back section of the pants, which layer includes an elastically stretchable web material. Suitable elastic materials are different types of elastic nonwoven material. An elastic nonwoven material that is suitable for use in absorbent pants shall can be extended elastically at least 80% or at least 100% in the transverse direction of the pants to obtain a sufficiently elastic fit around the edges of the leg openings on the front section. Furthermore, it is advantageous if the elastic nonwoven material can extend elastically also in the longitudinal direction of the absorbent pants, i.e. in a direction perpendicular to the transverse direction. Such a laminate yields elastic and breathable pants. It is also possible to use other, for example breathable, elastic materials. For example, so-called SMS material can be used. An SMS material is a nonwoven laminate with a layer of spunbond nonwoven on each side of a meltblown nonwoven layer.

According to another embodiment, the pant part is formed of a covering layer that includes an elastic laminate including at least one plastic film and one textile-like layer, which are connected to one another. It can be advantageous, however, if the plastic film has a certain breathability, i.e. permits the passage of water vapour through the layer to give the wearer increased comfort during use.

The elastic laminate can be composed of a first and a second outer layer of fibre material, with an elastic film layer situated between said fibre layers.

The outer fibrous layers are selected so that, in combination with the intermediate elastic film layer, they give the laminate a high resistance to puncturing. It also gives a soft and fabric-like feel to the laminate. The weight per unit area of the fibre material layers should be between 10 and 35 g/m$^2$, between 12 and 30 g/m$^2$ or between 15 and 25 g/m$^2$.

Examples of suitable polymers that are used in the fibre material are polyethylene, polyesters, polypropylene and other homopolymers and copolymers.

Natural fibres, e.g. cotton, can also be used as long as they provide the required properties.

According to one embodiment, the intermediate layer is a perforated elastic film that has a weight per unit area of between 20 and 100 g/m$^2$, or of between 20 and 60 g/m$^2$.

The film can be of any suitable elastic polymer, natural or synthetic. Some examples of suitable materials for the elastic film are low-crystalline polyethylene, metallocene-catalysed low-crystalline polyethylene, ethylene vinyl acetate copolymers (EVA), polyurethane, styrene copolymers, styrene segment copolymers such as styrene/isoprene/styrene (SIS), styrene/butadiene/styrene (SBS) or styrene/ethylene-butadiene/styrene segment copolymers.

Blends of these polymers can also be used, as well as other modified elastomer or non-elastomer materials.

An example of a suitable film is a perforated three-layer elastomer film of PE-SEBS-PE.

The elastic laminate can be produced in accordance with a modified version of the method that is described in WO 03/047488, in which the spunbonded layer is applied to the film in an adhesive state and thus creates a bond with the film layer, while the other spunbonded layer is adhesively laminated to the film layer by using a pressure-sensitive hot-melt adhesive, for example.

According to another embodiment, the pant part is formed of a covering layer including two layers with a plurality of intermediate elastic elements. Suitable elastic elements are different types of elastic threads, bands, elastic nonwoven, elastic foamed material or similar. A plurality of threads or the like are applied in a prestressed state transversely over both the front and back section. The transverse elastic elements are suitably enclosed between two layers of material, such as different types of nonwoven or other textile-like material, which material constitutes the covering layer of the article that forms the front and back section and crotch section of the pants.

The elastic elements can be coloured. Since the elastic threads lie principally crosswise over both the front and the back section, the article acquires a striped appearance, which can be felt to be more underwear-like. An example of elastic threads is sold under the LYCRA trademark. Other examples of suitable yarns include Dorlastan from Bayer AG and Linels from Fillatice.

According to another embodiment, the absorbent article includes a surface layer that is placed on the side of the core that faces the user when the article is worn. The surface layer is liquid-permeable and can be formed from any material known for the purpose, such as a layer of nonwoven material, perforated plastic film, net material, tow (parallel fibres) or similar. The laminate can naturally also include a laminate of two or more layers of the same or different material.

According to another embodiment, the extension of the surface layer coincides with the extension of the covering layer. The surface layer will be regarded as constituting a part of the pant part in the case of said embodiment. In this embodiment, it is important that the covering layer is formed of a thin and air-permeable material to prevent the pants from becoming too dense and less comfortable to wear. It is also important that the colour is adjusted to a slightly lighter shade on the barrier layer when the extension of the surface layer corresponds to the extension of the covering layer, in order to compensate for the influence of the surface layer on how much the skin shows through the pant part. Seen from the outside of the article, the barrier layer will be covered by a layer that corresponds to the extension of the covering layer, while the wearer's skin will be covered by two layers, which corresponds to the covering layer and also the extension of the surface layer.

The covering layer suitably includes a conventional liquid-permeable material. Examples of suitable materials are perforated plastic films, nonwoven material, plastic mesh or the like.

The materials that are suitable as a covering layer should be soft and non-irritating to the skin and can easily be penetrated by bodily fluid, e.g. urine.

With regard to the aforesaid embodiment, it is expedient that the covering layer is connected to the surface layer to prevent the article from being felt to be baggy or looking more nappy-like in appearance. The surface layer and the covering layer can expediently be joined by ultrasonic technology, adhesive or the like. When using adhesive, it is advisable to use a grade that does not appreciably have any colour.

According to another embodiment, the pant part has a base colour. As used herein, the term "base colour" means the colour that substantially constitutes the largest area of the extension of the pant part.

The base colour can include a primary colour such as white, black, red, blue, violet, orange, yellow, green and indigo, as well as any other hue or mix thereof.

The colour can be added to the material either upon manufacture of it or supplied afterwards by known print techniques. Examples of print technique can be flexography, ink-jet printers etc.

According to another embodiment, the pant part is covered with a graphic pattern to resemble conventional textile underwear as far as possible. To satisfy this requirement, the pants have been designed with a typical conventional pattern in colour, for example longitudinal stripes in grey, blue or brown to resemble men's underpants, or a more feminine pattern, such as flowers, butterflies and/or colours that are regarded more as being associated with women. If the graphic pattern constitutes the biggest area of the extension of the pant part, this is considered to form the pant part base colour.

Said embodiments are suitably packaged in consumer packaging, which includes a code that clearly indicates the skin tone in which the article has been designed to obtain best discretion. The consumer packaging can be packaging containing one or a number of articles. This code can be formed of a shade, which corresponds to the colour of the reference skin tone, a colour scale in colour in which the reference skin tone is depicted together with the surrounding skin tones, or it is stated in words which skin tone the article is designed for: wearers with a Light skin tone, Yellow/Red skin tone or Dark skin tone. Other illustrations on the outer packaging as guidance for the wearer to the right article can be a drawn figure in the shape of a person, for example, or the like having the intended skin tone (as well as nearby skin tones) that the article is intended to match.

Somewhere on the outer packaging it is appropriately illustrated what articles there are in this range for different skin tones to make the range clearer and to enable the wearer to compare and more easily find the most suitable article for maximum discretion.

DETAILED DESCRIPTION OF PARTICULAR EMBODIMENTS

Figure 1:
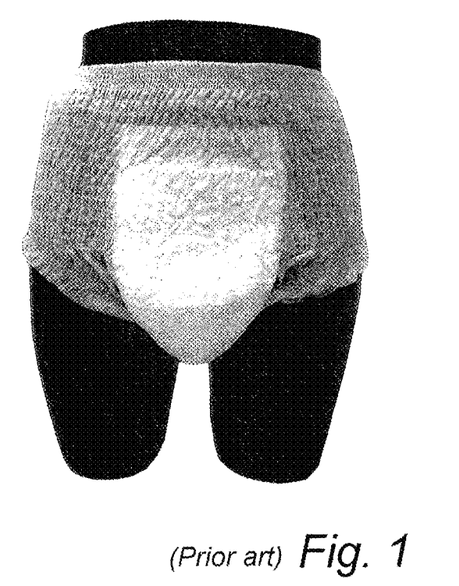
FIG. 1 is a photograph showing a dark-skinned mannequin from the front wearing an article in the form of pants of the prior art

FIG. 1 shows a photograph showing a dark-skinned mannequin seen from the front wearing an article in the form of pants of the prior art, namely TENA Pants. The pant part includes a covering layer, which is formed of a laminate including two inelastic nonwoven layers in which elastic Spandex threads are placed between these. The two nonwoven layers are sealed to one another with sealing adhesive. The two nonwoven layers are formed of hydrophobic spunbond and have a weight per unit area of 18 and 16 $g/m^2$ respectively. The two nonwoven layers are white in colour and thus have a base colour that is white in colour. The pant part has an opacity that is 48%, which means that the skin tone of the mannequin is clearly visible through the pant part. The area of the barrier layer that is placed in the area of the absorbent core between the absorbent core and the covering layer also appears clearly. The barrier layer is formed of a white plastic film of polyethylene with the weight per unit area 22 $g/m^2$ with a measured $L^*$, $a^*$, $b^*$ value of $L^*=94.1$, $a^*=0.02$ and $b^*=1.68$. The colour difference in the article between the area of the extension of the barrier layer and at least the closest adjacent area to the barrier layer is substantial. The reason for this is that the barrier layer has a colour that greatly differs from the skin tone of the mannequin.

The pant part includes a core of cellulose fibres and superabsorbent material that is placed in the crotch section and further over the front section and back section of the pant part. The extension of the barrier layer covers the extension of the core.

The article is also provided with a surface layer of nonwoven material, the extension of which coincides with the extension of the barrier layer and they are sealed to one another at their peripheries.

Colour measurements and calculation of the difference in ΔE were carried out on the article in the areas of the low-opacity area of the pant part, which extends over and outside the extension of the barrier layer. The article that is shown in FIG. 1 fitted on a mannequin with dark skin tone was tested against a reference surface that has the following value $L^*=25.2$, $a^*=0.1$ and $b^*=-0.9$. The colour of the reference surface mirrors the colour of the mannequin.

The difference in ΔE was calculated as 28.8.

Visual assessments in normal light conditions carried out indoors indicated that a pant part that has an opacity of 48% should not have a ΔE value greater than 5 between measurements carried out on the pant part outside the extension of the barrier layer and the area over the extension of the barrier layer. A value of ΔE greater than 5 would mean that persons in the vicinity of the wearer can discern the difference in colour shades between the pant part outside the extension of the barrier layer and the area over the extension of the barrier layer. The article thus falls not within the scope of the invention.

Figure 2:
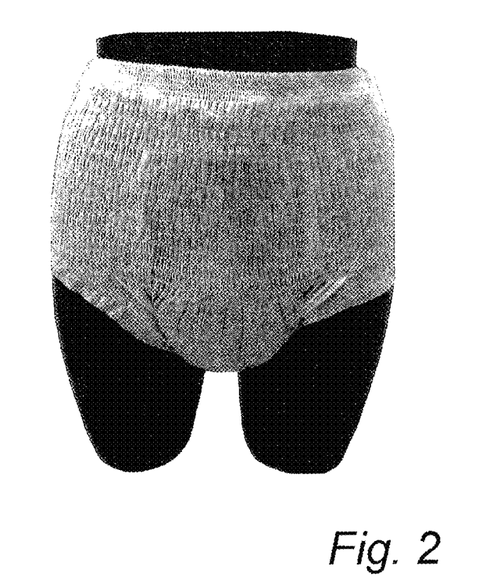
FIG. 2 is a photograph showing a dark-skinned mannequin from the front wearing an article in the form of pants in accordance with an embodiment described here

FIG. 2 shows a photograph with the same dark-skinned mannequin seen from the front wearing an article that corresponds to that illustrated in FIG. 1, except that the white barrier layer has been exchanged for a coloured barrier layer that is formed of a plastic film of polyethylene with a weight per unit area of 24 g/m² and a measured $L^*$, $a^*$, $b^*$ value of $L^*=27.0$, $a^*=0.4$, $b^*=0.5$ in accordance with the CIE $L^*a^*b^*$ standard method described. The coloured barrier layer was measured without an overlying covering layer.

A similar colour measurement and calculation were carried out on the article shown in FIG. 2 as described for the article shown in FIG. 1. The same reference surface that was used for the article shown in FIG. 1 was used for the measurement of the article shown in FIG. 2. The colour of the reference surface mirrors the colour of the mannequin.

The article shown in FIG. 2 was measured and calculated to be 3.3 in difference of ΔE in the areas of the low-opacity area of the pant part, which extends over the barrier layer and outside the extension of the barrier layer respectively. It is clearly evident in FIG. 2 how well suited the colour shade of the barrier layer is to a person with a dark skin tone such as that of the mannequin.

Visual assessments in normal light conditions carried out indoors indicated that a pant part that has an opacity of 48% should not have a ΔE value greater than 5 between measurements carried out on the pant part outside the extension of the barrier layer and the area over the extension of the barrier layer. A value of ΔE greater than 5 would mean that persons in the vicinity of the wearer can discern the difference in colour shades between the pant part outside the extension of the barrier layer and the area over the extension of the barrier layer. The article shown in FIG. 2 thus falls within the scope of an embodiment of the invention.

Figure 3:
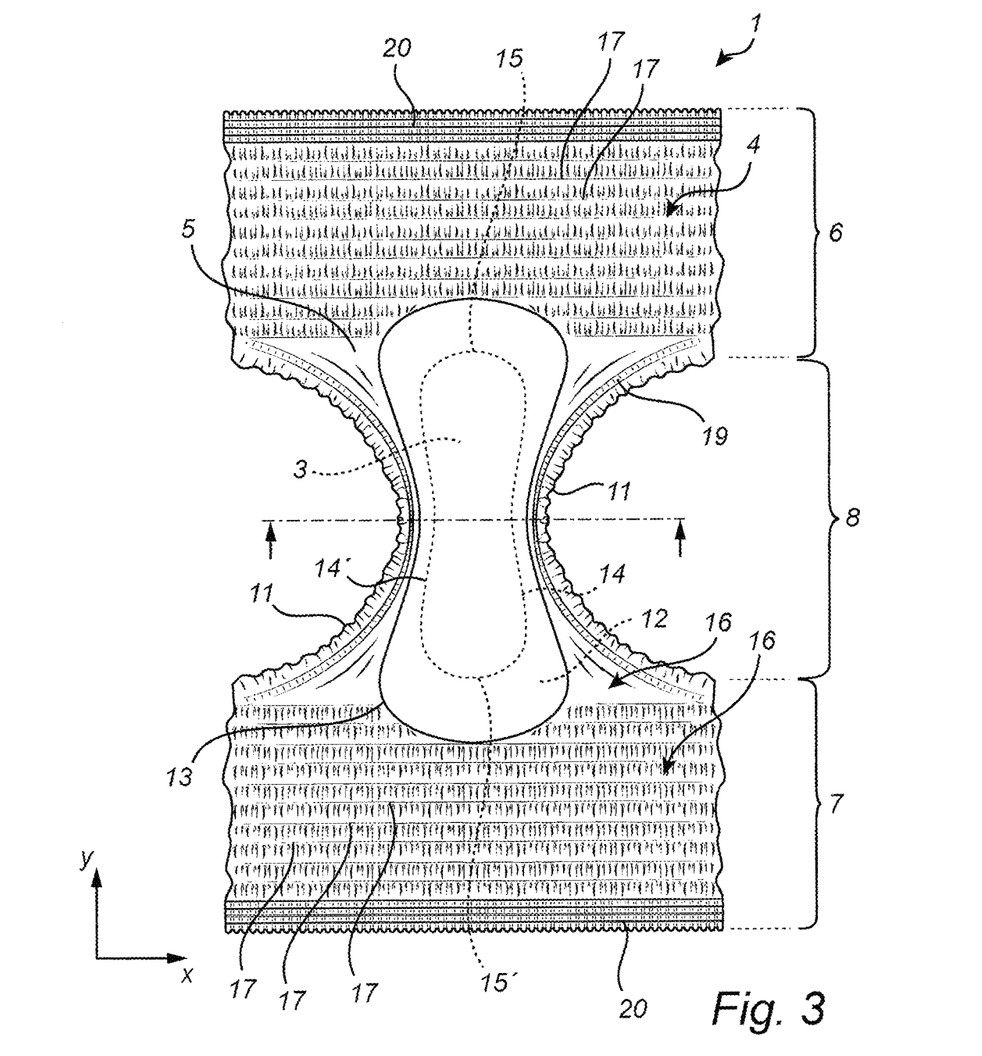
FIG. 3 is an article in the form of pants, in which the pants are present in a non-assembled state and are seen from the side that faces the wearer during use
Figure 4:
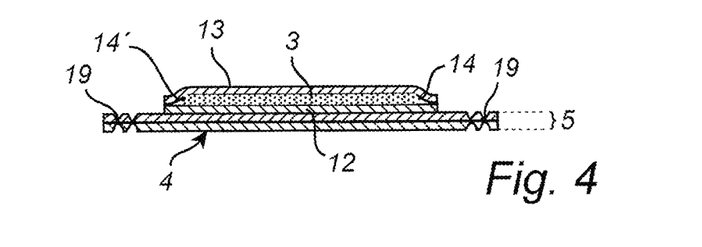
FIG. 4 is a section along the line X1 through the article in FIG. 3

FIGS. 3 and 4 show an embodiment of the article 1 in the form of pants, in which the pants are present in a non-assembled state. The article 1 lies extended with the upper side corresponding to the side intended to lie against the wearer during use. The article 1 is not restricted to use by adults for the absorption of various bodily secretions, but can also be intended for use by young people or by infants. The article 1 can also be intended as sanitary protection in the form of pants for absorption of menstrual fluid.

The absorbent article 1 has a pant part 4, which includes a covering layer 5 that is formed by a front section 6, a back section 7 and an intermediate crotch section 8. The crotch section 8 has a width that is narrower compared with the width of the front section 6 and back section 7 in order to be better adapted to the crotch area of the wearer. The article has a longitudinal direction Y and a transverse direction X. An absorbent core 3 having two longitudinal edges 14, 14' and two transverse edges 15, 15' is arranged mainly in the crotch section 8 and connected to the covering layer 5 on the side of the covering layer 5 that is intended to face the wearer.

The core 3 can advantageously be connected to the covering layer 5 by any form of construction adhesive. Said core 3 has an hourglass-shaped appearance but can also be shaped in different ways. Other shapes of the core can be rectangular, teardrop-shaped, triangular, T-shaped, H-shaped, oval or similar. The core 3 includes absorbent cellulose fibres and superabsorbent material.

The pant part 4 includes a covering layer 5, which is formed here of a laminate including two inelastic nonwoven layers where elastic threads 17 have been placed between them. The elastic threads 17 are laid crosswise in the transverse direction of the article, i.e. on the X-X line of the article. Examples of elastic threads 17 are sold under the LYCRA or SPANDEX trademark.

The two nonwoven layers are formed from hydrophobic spunbond and have a weight per unit area of 18 and 16 g/m² respectively.

The two nonwoven layers are connected to one another by construction adhesive by coating the elastic threads 17 between the nonwoven layers using the "V-slot technique", for example. A suitable construction adhesive is "Adhesive Hotmelt", for example, from Henkel Adhesives, HB Fuller or Bostik. A suitable elastic adhesive is Dispomelt 723U from Henkel Adhesives, for example. It is naturally possible to join the nonwoven layers in the integral covering layer 5 by a plurality of individual weld points. Ultrasonic welding is a suitable method for the purpose.

The two nonwoven layers are white in colour and thus have a base colour that is white in colour. Examples of other laminates that have an opacity of lower than 50% are described under the heading "Articles included in the laboratory measurements", articles B-E.

Said pant part 4 in this example embodiment according to FIG. 3 has an opacity that is 48%. The article 1 further includes a liquid-tight coloured barrier layer 12 that is placed between said absorbent core 3 and the covering layer 5. The barrier layer 12 is expediently connected to the covering layer 5 by adhesive. The barrier layer 12 has a colour which corresponds in principle to a predetermined skin tone. Since the pant part 4 has an opacity that is 48% over the area of the extension of the barrier layer 12 and also outside the extension of the barrier layer 12, the wearer's skin will show through the pant part 4 outside the extension of the barrier layer 12 and the coloured barrier layer 12 will show through the pant part 4 in such a way that it creates an illusion that the colour/colour shade of the barrier layer 12 corresponds to the wearer's skin. The colour/colour shade of the individual barrier layer 12, the colour/colour shade that is measured on the barrier layer 12 without the influence of the covering layer 5, has an $L^*$ value of 30.1-67.9, an $a^*$ value of 5.5-7.0 and a $b^*$ value of 7.5-20.3. This span of colour shade of the barrier layer 12 is intended to cover "Light skin tone", "Yellow/red skin tone" and "Dark skin tone".

The colour/colour shade selected for the barrier layer 12 thus depends on the skin tone that it is desired that the product is intended for.

The extension of the barrier layer 12 in a plane is slightly greater compared with the absorbent core 3, in order to conceal the core 3 effectively and to contribute to the leakage security. According to the example, the barrier layer 12 has the same outer shape as the absorbent core 3. This is not the most important thing, but the important thing is that the barrier layer 12 covers the whole of the extension of the core 3.

A surface layer 13 that corresponds to the extension of the barrier layer 12 to a large extent is placed on top of the core that faces the wearer during use. The barrier layer 12 and the surface layer 13 have a slightly larger extension in one plane compared with the extension of the core 3, which means that the barrier layer 12 and the surface layer 13 form a projecting edge around all the edges 15, 15', 14, 14' of the core. This is seen clearly in FIG. 4. The barrier layer 12 and the surface layer 13 are joined to one another, for example by gluing, sewing, or welding using heat or ultrasound, which means that the core 3 is enclosed between the barrier layer 12 and the surface layer 13.

The surface layer 13 is liquid-permeable and is formed in this case of a spunbonded, 16 g/m², hydrophilic material. The invention is not restricted to a specific surface layer, but can be formed of any material known for the purpose, such as a layer of nonwoven material, perforated plastic film, net material, tow (parallel fibres) or the like. The laminate can naturally also include a laminate of two or more layers of the same or different materials.

The article 1 was designed with waist elastic 20 at the front 6 and back 7 edges of the pant part, which form the waist opening 10 of the article, and at the crotch section 8 of the pant part, which forms the leg openings of the article, here called leg elastic 19, to further improve the fit of the article 1 against the wearer's body. The waist elastic 20 is laid crosswise in the transverse direction of the article, i.e. on the X-X line of the article. Examples of elastic threads are sold under the Spandex trademark.

Figure 5:
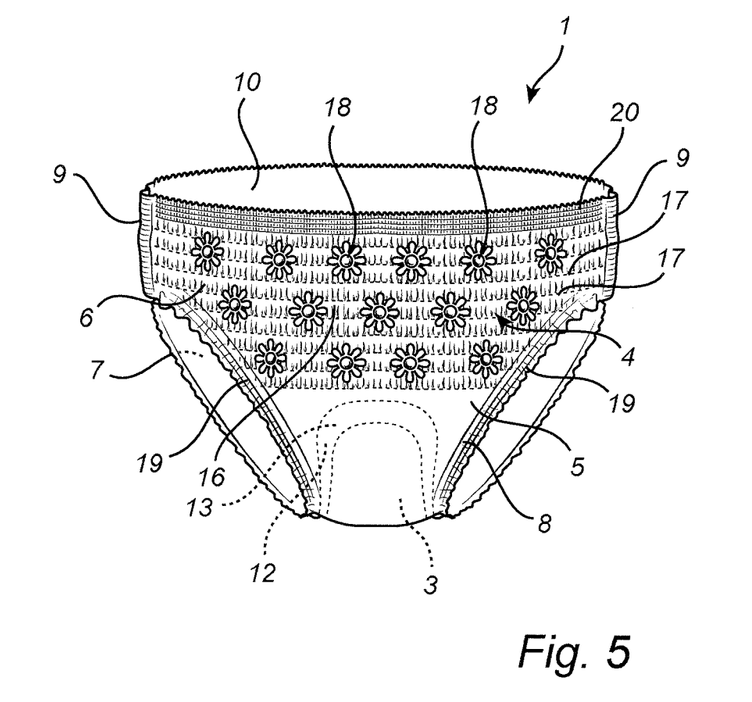
FIG. 5 is an article in the form of pants in which the article is present in an assembled state

According to FIG. 5, an article is shown in the form of pants, which corresponds to the article in FIGS. 3 and 4, but in an assembled state. Here it emerges clearly how the front section 6 and back section 7 are joined to one another in a seam 9. The seam 9 can be provided by mechanical processing, for example, thermal treatment or another well-known technique for joining materials to one another. Naturally adhesive can also be used to connect the front and back sections to one another. In the figure the waist area 10 also stands out clearly and the leg openings 11, which are formed after the article has been assembled. The covering layer 5 of the article has been provided on the side facing away from the wearer with a graphic pattern 18. The pattern 18 includes a number of small flowers, which have been distributed uniformly over the entire extension of the surface, i.e. the distance between each flower is the same for all flowers in the composed graphic pattern 18. The graphic pattern 18 can naturally include one or just a few sporadically positioned ornaments over the extension of the covering layer 5. The graphic pattern 18 can include one colour or several colours. In this particular embodiment, the graphic pattern 18 does not constitute the greatest area of the pant part 4 extension and is thus not considered to constitute the base colour of the pant part 4.

Description of Method of Opacity Measurement
Opacity

Opacity is measured in accordance with ISO 2471:2008 "Paper and board—Determination of opacity (paper backing)—Diffuse reflectance method". The method is designed to measure the opacity of paper, but has been found suitable also in this context. The opacity is measured on the pant part 4 in its unstretched state. If the pant part 4 includes different materials, structure or for example an irregular base colour or graphic pattern 18 in different areas, measurements should be carried out over all areas of the pant part 4.

Measuring Equipment

Opacity can be measured using a reflectometer or spectrophotometer. An example of a spectrophotometer is model CM-5 from Konica-Minolta (Japan). A suitable diameter of the recording aperture is 30 mm in diameter. If the surface that is to be measured has a fine pattern 18, it may be necessary to select a recording aperture that is less than 30 mm in diameter.

Sample Preparation

Since the absorbent article 1 is in the form of pants, the sides, of which the front section 6 and back section 7 have been joined in a seam 9, are torn/clipped.

Test Procedure

The pant part with the surface of interest is placed over the recording aperture of the instrument. If the pant part 4 has several areas that appear to have different opacity in their extension, measurements are to be taken on all areas. The measurement can then commence.

Calculation of Opacity Value

The measured opacity value for the pant part 4 is a mean value from 3 measurements in the same area. If the pant part 4 includes different materials, structure or for example an irregular base colour or graphic pattern 18 in different areas, a mean value is derived from 3 measurements for the respective areas.

The results are indicated with an accuracy in whole numbers.

Method Description of Measurement of L* a* and b* Value and ΔE Value Principle

Colour is measured according to a standard procedure from CIE (Commission Internationale de l'Eclairage), defined in 1976. The colour space is divided into three axes. L* represents lightness and the axis extends from 0 (black) to 100 (white). The axis a* goes from green to red, where positive values indicate more measured red, and negative values more measured green. The b* axis goes from blue to yellow, where positive values represent more measured yellow and negative values more measured blue. This colour space is well known in industry and is generally referred to as CIE L*a*b* or CIELAB (1976).

Measuring Equipment

Measurements are taken with a spectrophotometer. An example of a suitable apparatus is the "Spectrophotometer CM-5" from Minolta (Japan) with accompanying manual. Light source D65 is used, and the observation angle 10°. The instrument is set to "SCE" (Specular Component Excluded).

A suitable diameter of the recording aperture is 30 mm in diameter. If the surface that is to be measured has a fine pattern, it may be necessary to select a recording aperture that is less than 30 mm in diameter.

In measurements and calculation of the colour difference between article 1 in the area outside and within the area of the extension of the barrier layer 12, three different reference surfaces are used, "Light skin tone", "Yellow/red skin tone" and "Dark skin tone" from the "PANTONE SkinTone™ Guide-STG-201" colour chart.

"Light skin tone" is represented by the reference skin tone 5Y04 that has the following L*, a*, b* value; L*=67.9 a*=5.5 and b*=16.4.

"Yellow/red skin tone" is represented by the reference skin tone 4Y10 and has the following L*, a*, b* value; L*=52.6 a*=7.0 and b*=20.3.

"Dark skin tone" is represented by the reference skin tone 2R15 and has the following L*, a*, b* value; L*=30.1 a*=5.8 and b*=4.5.

Sample Preparation Before Measurement of the Colour Shade of the Barrier Layer

Since the absorbent article 1 is in the form of pants, the sides, of which the front section 6 and back section 7 have been joined in a seam 9, are torn/clipped. The article 1 is placed down flat against a table, for example, without stretching the article 1. The material/materials that form the pant part 4 is/are carefully removed from the barrier layer 12 to facilitate the laboratory measurement directly against the surface of the barrier layer 12. If it should be shown that the barrier layer 12 has a different structure or for example an irregular base colour or graphic pattern 18 in different areas, measurements should be taken over the surface that takes up the largest area of the barrier layer 12.

If several colours are found in exactly the same proportions on the surface of the barrier layer 12, i.e. no single colour covers a greater area than any other colour, the barrier layer 12 is represented by a mean value. The respective colour fields are each measured, and a mean value is calculated for the three respective axes L*, a* and b*.

Test Procedure when Measuring the Colour Shade of the Barrier Layer.

The recording aperture of the instrument is placed against the barrier layer 12. The measurement can then begin.

Calculation of the Colour Shade of the Barrier Layer

The measured L* a* and b* values for the barrier layer 12 are a mean value from 3 measurements.

The results are indicated accurate to one decimal point.

Sample Preparation Before Measurement of the Colour Difference Between the Article in the Area Outside and within the Area of the Extension of the Barrier Layer.

Since the absorbent article 1, in this embodiment, is nappy pants, the sides, of which the front section 6 and back section 7 are joined in a seam 9, are torn/clipped.

The article 1 is placed down flat against a table, for example, without stretching out the article, with the covering layer 5 facing downwards. The surface of the pant part 4 that extends outside the areas outside the extension of the barrier layer 12 that has an opacity that is lower than 50% is included in the measurement. If the pant part 4 includes areas that extend outside the barrier layer 12 with different opacity values, only the area with the lowest opacity shall be included in the measurement.

Aforesaid surface of the pant part 4 is to be compared with measurements taken on the surface of the pant part 4, the area of which lies directly above the barrier layer 12. If the pant part 4 has a different structure, or irregular base colour or graphic pattern 18 in different areas, for example, measurements should be taken over the surface that takes up the greatest area. In cases where the pant part is finely patterned (has fields with a diameter of less than 30 mm), it is advisable to select a smaller recording aperture on the spectrophotometer. If several colours exist in exactly the same proportions, i.e. no single colour covers a greater area than any other colour, the pant part is represented by a mean value.

The respective colour fields are each measured and a mean value calculated for the three respective axes L*, a* and b*. If the barrier layer 12 has a different structure, or irregular base colour or graphic pattern 18 in different areas, for example, this can affect the outcome of the measured colour shade for the area of the pant part 4 that lies directly above the extension of the barrier layer 12. A similar procedure must then be followed corresponding to that described for the pant part 4 that does not have a regular structure, base colour or graphic pattern 18.

If the barrier layer 12 has a different structure or irregular base colour or graphic pattern 18 in different areas, for example, this can affect the outcome of the measured colour shade for the area of the pant part that lies directly above the extension of the barrier layer 12.

Test Procedure

The surface of the pant part 4 that is of interest is placed on top of the reference surface "Light skin tone", "Yellow/red skin tone" and "Dark skin tone" in turn with the covering layer 5 facing upwards. The recording aperture of the instrument is placed against the pant part 4. The measurement can then begin.

Measurements are taken in the area of the extension of the barrier layer 12 and outside the extension of the barrier layer 12.

Calculation of the Difference

The measured colours/colour shades for respective areas of the pant part 4 are a mean value from 3 measurements.

The difference between the colour shade in the area of the extension of the barrier layer 12 and outside the extension of the barrier layer 12 is thus calculated according to: a difference between two colours in the colour space CIE L*a*b* being characterised by a Delta E-value ($\Delta E^*ab$). The differences between the colours on the three respective axes are squared in this, following which the differences are summed and the root derived from the sum: $\Delta E^*ab = ((\Delta L^*)^2 + (\Delta a^*)^2 + (\Delta b^*)^2)^{0.5}$.

The result is indicated accurate to one decimal point.

Articles that were Included in Various Laboratory Tests

Detailed description of articles A-E. The embodiments A-E represent examples of articles and must not be seen as any restriction on embodiments.

A1) is an article in the form of pants of the prior art, which are shown in FIG. 1, Tena Pants plus. The pant part 4 includes a covering layer 5, which is formed of a laminate including two inelastic nonwoven layers, where elastic Spandex threads 17 are placed between these. The two nonwoven layers are sealed to one another with sealing adhesive.

The two nonwoven layers are formed of hydrophobic spunbond and have a weight per unit area of 18 and 16 $g/m^2$ respectively. The barrier layer 12 is formed of a white plastic film of polyethylene with a weight per unit area of 22 $g/m^2$ with a measured L*, a*, b* value of L*=94.1, a*=0.02 and b*=1.68. The pant part 4 includes a core 3 of cellulose fibres and superabsorbent material that is placed in the crotch section 8 and further over the front section 6 and back section 7 of the pant part. The extension of the barrier layer 12 covers the extension of the core 3.

The article is also provided with a surface layer 13 of nonwoven material, the extension of which coincides with the extension of the barrier layer 12 and they are sealed to one another at their peripheries. The surface layer 13 is liquid-permeable and is formed in this case of a spunbonded, 16 $g/m^2$, hydrophilic material. Since the extension of the surface layer 13 coincides with the extension of the barrier layer 12 and they are sealed to one another at their peripheries, the surface layer 13 does not affect the opacity of the pant part 4.

A2) corresponds to reference article A1) described above except that the white barrier layer 12 has been exchanged for a coloured barrier layer 12 that is formed of a plastic film of polyethylene with a weight per unit area of 24 g/m² with a measured L*, a*, b* value of L*=27.0, a*=0.4, b*=0.5 in accordance with the CIE L*a*b* standard method described. The coloured barrier layer 12 is measured without an overlying covering layer 4. This article is illustrated in FIG. 2.

B) Article B corresponds to article A, except that the pant part 4, in this case includes an inelastic nonwoven, which is formed of a spunbond from Union with a weight per unit area of 16 g/m². The barrier layer 12 is formed of a coloured sheet which has been picked from said colour chart "PANTONE SkinTone™ Guide-STG-201". The article has been designed with a number of different colour shades of the barrier layer 12, which are shown clearly in tables III, IV and V.

C) Article C corresponds to article A except that the pant part 4, in this case, includes an inelastic nonwoven with the name S-Tex from Fitesa with a weight per unit area of 20 g/m². The barrier layer 12 is formed of a coloured sheet which has been picked from said "PANTONE SkinTone™ Guide-STG-201" colour chart. The article has been designed with a number of different colour shades of the barrier layer 12, which are shown clearly in tables III, IV and V.

D) Article D corresponds to article A, except that the pant part 4, in this case, includes three inelastic nonwovens of spunbond from Union, each with a weight per unit area of 16 g/m². The total weight per unit area is 48 g/m². The barrier layer 12 is formed of a coloured sheet which has been picked from said colour chart "PANTONE SkinTone™ Guide-STG-201". The article has been designed with a number of different colour shades of the barrier layer 12, which are shown clearly in tables III, IV and V.

E) Article E corresponds to the description of article A, except that the pant part 4, in this case, includes an inelastic nonwoven in three layers from Fitesa, each with a weight per unit area of 25 g/m². The total weight per unit area of the laminate is 75 g/m². The barrier layer 12 is formed of a coloured sheet which has been picked from said colour chart "PANTONE SkinTone™ Guide-STG-201". The article has been designed with a number of different colour shades of the barrier layer 12, which are shown clearly in tables III, IV and V.

All articles described here above are formed of nonwoven, which is naturally white in colour, i.e. they have not been coloured or provided with anything other than titanium dioxide pigment. The articles have been provided with graphic pattern 18 such as that described and illustrated in FIG. 5. The pattern 18 includes a number of small flowers, which have been distributed uniformly over the entire extension of the surface, i.e. the distance between each flower is the same for all flowers in the composed graphic pattern 18. In this example embodiment the graphic pattern 18 does not constitute the largest area of the extension of the pant part 4 and is thus considered not to constitute the base colour of the pant part 4. The base colour of the pant part 4 is formed of the natural whitish colour of the covering layer 5.

Measurement of the Opacity of the Articles A1-E3

TABLE 1

| Article | Opacity % |
| --- | --- |
| A1 and A2 | 48 |
| B | 15 |

TABLE 1-continued

| Article | Opacity % |
| --- | --- |
| C | 24 |
| D | 36 |
| E | 45 |

In table 1 it can be seen that all pant parts 4 are formed of material that has areas that have an opacity that is lower than 50% and thus they exemplify materials and combinations of materials that are contained within the scope of embodiments of the invention.

Comparing Measurements Taken on A1 and A2

The following articles, A1 and A2 that were shown in the FIGS. 1 and 2 fitted on a mannequin with dark skin tone, were tested against a reference surface that has the following value: L*=25.2, a*=0.1 and b*=−0.9. The colour of the reference surface corresponds to the colour of the mannequin. Measurements were taken of the extension of the pant part 4, which extends outside the barrier layer 12 and within the extension of the barrier layer 12.

The difference in ΔE is calculated between the value obtained outside and over the area of the barrier layer 12 respectively.

TABLE II

| Article | Colour shade measured on covering layer of pant part outside barrier layer extn | | | Colour shade measured on covering layer of pant part over area of barrier layer extension | | | Difference in ΔE in area outside and over barrier layer |
| --- | --- | --- | --- | --- | --- | --- | --- |
| | L* | a* | b* | L* | a* | b* | |
| A1 | 66.4 | 0.0 | 0.7 | 94.5 | 0.0 | 1.6 | 28.1 |
| A2 | 66.4 | 0.0 | 0.7 | 63.1 | 0.1 | 0.4 | 3.3 |

Said pant part for articles A1 and A2 has an opacity of 48%. Visual assessments in normal light conditions carried out indoors indicated that a pant part that has an opacity of between 40 and 50% should not have a ΔE value greater than 5 between measurements carried out on the pant part 4 outside the extension of the barrier layer 12 and the area over the extension of the barrier layer 12. A value of ΔE greater than 5 would mean that persons in the vicinity of the wearer can discern the difference in colour shades between the pant part 4 outside the extension of the barrier layer 12 and the area over the barrier layer 12. The article A1 is thus experienced as less discreet and nappy-like.

The product A2 was measured and calculated to be 3.3 in difference of ΔE in the area outside and over the barrier layer 12. It is clearly evident in FIG. 2 how well suited the colour shade of the barrier layer 12 is to a person with a dark skin tone such as that of the mannequin.

The difference in ΔE in the area outside and over the barrier layer 12 for article A1 is 28.1. It is clear from FIG. 1 how clearly the white barrier layer 12 is visible through the low-opacity pant part 4 at the same time as the mannequin's skin is visible through the pant part 4 outside the extension of the barrier layer 12.

Comparing Measurements Taken on the Articles B-E

In the tables III, IV and V below, the articles B-E were provided with different barrier layers 12 of different colour shades. The articles were measured against a defined reference surface, which should correspond to the skin tone that it is intended that the article is to be used for. In the tables III, IV and V below, values for what is considered to be an "Accepted difference in ΔE" in the area outside and over the barrier layer 12 are entered, so that the article shall be judged to yield acceptable discretion during use. As stated previously, this value "Accepted difference in ΔE" was produced by visual assessments under normal light conditions indoors. The values of the pant parts 4 of the articles relating to the opacity values are represented in the table.

Table III shows measurements taken on the articles B-E. The articles were designed with some randomly selected barrier layers 12: 5Y04, 1R02, 3Y03, 4Y10 and 2R15 picked from the aforesaid colour chart "PANTONE SkinTone™ Guide-STG-201". The articles were measured according to the method above against a predetermined reference surface 5Y04, which colour shade mirrors a wearer with a light skin tone.

Table IV shows measurements taken on the articles B-E. The articles were designed with some randomly selected barrier layers 12: 4Y10, 2R10, 3Y09, 5Y04 and 2R15 picked from the aforesaid colour chart "PANTONE SkinTone™ Guide-STG-201". The articles were measured according to the method above against a predetermined reference surface 4Y10, which colour mirrors a wearer with yellow/red skin tone.

Table V shows measurements taken on the articles B-E. The articles were designed with some randomly selected barrier layers 12: 2R15, 1R14, 4R15, 5Y05 and 4Y10 picked from the aforesaid colour chart "PANTONE SkinTone™ Guide-STG-201". The articles were measured according to the method above against a predetermined reference surface 2R15, which colour mirrors a wearer with a dark skin tone.

In the tables it is clearly evident that the difference in ΔE in the area outside and over the barrier layer 12 of the article reduces as the opacity of the pant part 4 increases. This means that a barrier layer 12 with a certain colour shade can suit several wearers with a broader skin tone difference when the pant part 4 is formed of a higher opacity value compared with if the pant part 4 has a lower opacity.

Furthermore, it can be seen from Table III, for example, that two articles with the barrier layer 12 5Y04 and 4Y10 fall within the scope of "Accepted difference in ΔE" in the area outside and over the barrier layer 12 when the opacity of the pant part 4 is 15% and when the pant part 4 has 45% there are four articles with the following barrier layer 12 5Y04, 1R02, 3Y03 and 4Y10 that are considered visually acceptable.

TABLE III

Samples B-E measured against reference surface 5Y04 (light skin tone)

| Article with different shades of barrier layer | Measured opacity of covering layer of pant part | Accepted difference in ΔE in area outside and over barrier layer Visual assessment | Colour shade of Light skin tone (5Y04) observed through covering layer of pant part | | | Colour shade of barrier layer observed through covering layer of pant part | | | Difference in ΔE in area outside and over barrier layer |
|---|---|---|---|---|---|---|---|---|---|
| | % | ΔE | L* | a* | b* | L* | a* | b* | ΔE |
| B-5Y04 | 15 | <2 | 70.5 | 4.5 | 11.5 | 70.5 | 4.5 | 11.5 | 0.0 |
| B-1R02 | 15 | <2 | 70.5 | 4.5 | 11.5 | 71.8 | 6.9 | 9.5 | 3.4 |
| B-3Y03 | 15 | <2 | 70.5 | 4.5 | 11.5 | 71.4 | 5.7 | 11.1 | 1.6 |
| B-4Y10 | 15 | <2 | 70.5 | 4.5 | 11.5 | 60.3 | 4.5 | 10.6 | 10.2 |
| B-2R15 | 15 | <2 | 70.5 | 4.5 | 11.5 | 49.9 | 2.1 | 2.2 | 22.8 |
| C-5Y04 | 24 | <3 | 73.2 | 3.2 | 7.9 | 73.2 | 3.2 | 7.9 | 0.0 |
| C-1R02 | 24 | <3 | 73.2 | 3.2 | 7.9 | 74.4 | 5.7 | 6.7 | 2.7 |
| C-3Y03 | 24 | <3 | 73.2 | 3.2 | 7.9 | 74.0 | 4.8 | 7.8 | 1.4 |
| C-4Y10 | 24 | <3 | 73.2 | 3.2 | 7.9 | 65.1 | 3.2 | 5.6 | 8.4 |
| C-2R15 | 24 | <3 | 73.2 | 3.2 | 7.9 | 57.4 | 0.6 | −1.5 | 18.5 |
| D-5Y04 | 36 | <4 | 77.2 | 2.6 | 5.7 | 77.2 | 2.6 | 5.7 | 0.0 |
| D-1R02 | 36 | <4 | 77.2 | 2.6 | 5.7 | 77.8 | 3.9 | 5.0 | 1.6 |
| D-3Y03 | 36 | <4 | 77.2 | 2.6 | 5.7 | 77.7 | 3.4 | 5.7 | 0.9 |
| D-4Y10 | 36 | <4 | 77.2 | 2.6 | 5.7 | 72.4 | 2 | 4.1 | 5.1 |
| D-2R15 | 36 | <4 | 77.2 | 2.6 | 5.7 | 68.6 | 0.7 | 0.7 | 10.1 |
| E-5Y04 | 45 | <5 | 80.6 | 1.9 | 4.0 | 80.6 | 1.9 | 4.0 | 0.0 |
| E-1R02 | 45 | <5 | 80.6 | 1.9 | 4.0 | 81.0 | 2.8 | 3.5 | 1.0 |
| E-3Y03 | 45 | <5 | 80.6 | 1.9 | 4.0 | 80.9 | 2.5 | 4 | 0.6 |
| E-4Y10 | 45 | <5 | 80.6 | 1.9 | 4.0 | 77.2 | 1.4 | 2.6 | 3.7 |
| E-2R15 | 45 | <5 | 80.6 | 1.9 | 4.0 | 74.9 | 0.4 | 0.4 | 6.9 |

TABLE IV

Samples B-E measured against reference surface 4Y10 (yellow/red skin tone)

| Article with different shades of barrier layer | Measured opacity of covering layer of pant part | Accepted difference in ΔE in area outside and over barrier layer Visual assessment | Colour shade of Yellow/red skin tone (4Y10) observed through covering layer of pant part | | | Colour shade of barrier layer observed through covering layer of pant part | | | Difference in ΔE in area outside and over barrier layer |
|---|---|---|---|---|---|---|---|---|---|
| | % | ΔE | L* | a* | b* | L* | a* | b* | ΔE |
| B-4Y10 | 15 | <2 | 60.3 | 4.5 | 10.6 | 60.3 | 4.5 | 10.6 | 0.0 |
| B-2R10 | 15 | <2 | 60.3 | 4.5 | 10.6 | 60.1 | 9.2 | 10.2 | 4.8 |
| B-3Y09 | 15 | <2 | 60.3 | 4.5 | 10.6 | 62.2 | 6.6 | 11.1 | 2.7 |
| B-5Y04 | 15 | <2 | 60.3 | 4.5 | 10.6 | 7.1 | 4.5 | 11.5 | 10.2 |

TABLE IV-continued

Samples B-E measured against reference surface 4Y10 (yellow/red skin tone)

| Article with different shades of barrier layer | Measured opacity of covering layer of pant part | Accepted difference in ΔE in area outside and over barrier layer Visual assessment | Colour shade of Yellow/red skin tone (4Y10) observed through covering layer of pant part | | | Colour shade of barrier layer observed through covering layer of pant part | | | Difference in ΔE in area outside and over barrier layer |
|---|---|---|---|---|---|---|---|---|---|
|  | % | ΔE | L* | a* | b* | L* | a* | b* | ΔE |
| B-2R15 | 15 | <2 | 60.3 | 4.5 | 10.6 | 49.9 | 2.1 | 2.2 | 13.6 |
| C-4Y10 | 24 | <3 | 65.1 | 3.2 | 5.6 | 65.1 | 3.2 | 5.6 | 0.0 |
| C-2R10 | 24 | <3 | 65.1 | 3.2 | 5.6 | 65.0 | 7.0 | 5.4 | 3.8 |
| C-3Y09 | 24 | <3 | 65.1 | 3.2 | 5.6 | 66.6 | 4.7 | 6.3 | 2.2 |
| C-5Y04 | 24 | <3 | 65.1 | 3.2 | 5.6 | 73.2 | 3.7 | 7.9 | 8.4 |
| C-2R15 | 24 | <3 | 65.1 | 3.2 | 5.6 | 57.4 | 0.6 | −1.5 | 10.7 |
| D-4Y10 | 36 | <4 | 72.4 | 2.0 | 4.1 | 72.4 | 2.0 | 4.1 | 0.0 |
| D-2R10 | 36 | <4 | 72.4 | 2.0 | 4.1 | 72.3 | 4.1 | 4.1 | 2.1 |
| D-3Y09 | 36 | <4 | 72.4 | 2.0 | 4.1 | 73.1 | 3.0 | 4.6 | 1.3 |
| D-5Y04 | 36 | <4 | 72.4 | 2.0 | 4.1 | 77.2 | 2.6 | 5.7 | 5.1 |
| D-2R15 | 36 | <4 | 72.4 | 2.0 | 4.1 | 68.6 | 0.7 | 0.7 | 5.3 |
| E-4Y10 | 45 | <5 | 77.2 | 1.4 | 2.6 | 77.2 | 1.4 | 2.6 | 0.0 |
| E-2R10 | 45 | <5 | 77.2 | 1.4 | 2.6 | 77.4 | 2.7 | 2.6 | 1.4 |
| E-3Y09 | 45 | <5 | 77.2 | 1.4 | 2.6 | 77.9 | 2.0 | 3.0 | 0.9 |
| E-5Y04 | 45 | <5 | 77.2 | 1.4 | 2.6 | 80.6 | 1.9 | 4.0 | 3.7 |
| E-2R15 | 45 | <5 | 77.2 | 1.4 | 2.6 | 74.9 | 0.4 | 0.4 | 3.3 |

TABLE V

Samples B-E measured against reference surface 2R15 (dark skin tone)

| Article with different shades of barrier layer | Measured opacity of covering layer of pant part | Accepted difference in ΔE in area outside and over barrier layer Visual assessment | Colour shade of Dark skin tone (2R15) observed through covering layer of pant part | | | Colour shade of barrier layer observed through covering layer of pant part | | | Difference in ΔE in area outside and over barrier layer |
|---|---|---|---|---|---|---|---|---|---|
|  | % | ΔE | L* | a* | b* | L* | a* | b* | ΔE |
| B-2R15 | 15 | <2 | 49.9 | 2.1 | 2.2 | 49.9 | 2.1 | 2.2 | 0.0 |
| B-1R14 | 15 | <2 | 49.9 | 2.1 | 2.2 | 51.4 | 3.4 | 4.2 | 2.9 |
| B-4R15 | 15 | <2 | 49.9 | 2.1 | 2.2 | 49.9 | 2.4 | 2.3 | 0.3 |
| B-5Y05 | 15 | <2 | 49.9 | 2.1 | 2.2 | 70.5 | 4.5 | 11.5 | 22.8 |
| B-4Y10 | 15 | <2 | 49.9 | 2.1 | 2.2 | 60.3 | 4.5 | 10.6 | 13.6 |
| C-2R15 | 24 | <3 | 57.4 | 0.6 | −1.5 | 57.4 | 0.6 | −1.5 | 0.0 |
| C-1R14 | 24 | <3 | 57.4 | 0.6 | −1.5 | 58.5 | 1.6 | 0.0 | 2.1 |
| C-4R15 | 24 | <3 | 57.4 | 0.6 | −1.5 | 57.5 | 0.8 | −1.5 | 0.2 |
| C-5Y05 | 24 | <3 | 57.4 | 0.6 | −1.5 | 73.2 | 3.7 | 7.9 | 18.5 |
| C-4Y10 | 24 | <3 | 57.4 | 0.6 | −1.5 | 65.1 | 3.2 | 5.6 | 10.7 |
| D-2R15 | 36 | <4 | 68.6 | 0.7 | 0.7 | 68.6 | 0.7 | 0.7 | 0.0 |
| D-1R14 | 36 | <4 | 68.6 | 0.7 | 0.7 | 68.9 | 1.2 | 1.4 | 0.9 |
| D-4R15 | 36 | <4 | 68.6 | 0.7 | 0.7 | 68.4 | 0.8 | 0.7 | 0.2 |
| D-5Y05 | 36 | <4 | 68.6 | 0.7 | 0.7 | 77.2 | 2.6 | 5.7 | 10.1 |
| D-4Y10 | 36 | <4 | 68.6 | 0.7 | 0.7 | 72.4 | 2.0 | 4.1 | 5.3 |
| E-2R15 | 45 | <5 | 74.9 | 0.4 | 0.4 | 74.9 | 0.4 | 0.4 | 0.0 |
| E-1R14 | 45 | <5 | 74.9 | 0.4 | 0.4 | 75.4 | 0.8 | 0.9 | 0.7 |
| E-4R15 | 45 | <5 | 74.9 | 0.4 | 0.4 | 75.0 | 0.5 | 0.5 | 0.2 |
| E-5Y05 | 45 | <5 | 74.9 | 0.4 | 0.4 | 80.6 | 1.9 | 4.0 | 6.9 |
| E-4Y10 | 45 | <5 | 74.9 | 0.4 | 0.4 | 77.2 | 1.4 | 2.6 | 3.3 |

The invention claimed is:

1. An absorbent article in the form of pants comprising:

a pant part, wherein said pant part comprises a covering layer, a front section, a back section and an intermediate crotch section, wherein the front and back sections are connected to one another along two opposing longitudinal lateral edges to form a waist opening and a pair of leg openings, wherein said pant part comprises at least one low-opacity area, which has an opacity that is lower than or equal to 30%;

an absorbent core having two longitudinal edges and two transverse edges, said absorbent core being arranged in at least the crotch section and connected to the covering layer on the side of the covering layer that is intended to face the wearer such that the low-opacity area of said pant part covers at least a portion of the absorbent core; and a liquid-tight coloured barrier layer placed between said absorbent core and covering layer, extension of the barrier layer coinciding on the whole with extension of the absorbent core and at least a portion of the barrier layer is covered by the low-opacity area of said pant part, wherein said barrier layer has a skin-like colour with an L* value of 30.1-67.9, a* value of 5.5-7.0 and b* value of 7.5-20.3 in accordance with the CIE L*a*b* standard method, and wherein the difference between two colours in the colour space CIE L*a*b*, which is characterised by a Delta E-value (ΔE*ab) in a comparison between the low-opacity area/areas of the pant part covering the barrier layer and the low-opacity area/areas of the pant part outside the area of the barrier layer's extension is less than:

4 when said low-opacity area for the pant part has an opacity of 30%

3 when said low-opacity area for the pant part has an opacity of 20-30%

2 when said low-opacity area for the pant part has an opacity of 0-20%, when the absorbent article is placed with the side that is intended to face the wearer against a reference surface having a predetermined colour, in accordance with the CIEL*a*b* standard method, wherein the reference surface is formed of a surface that has the following L*, a*, b* value: L*=67.9 a*=5.5 and b*=16.4 or L*=52.6 a*=7.0 and b*=20.3 or L*=30.1 a*=5.8 and b*=4.5*, and wherein said pant part has a base colour that is different from the skin-like colour of said barrier layer.

2. The absorbent article according to claim 1, wherein the low-opacity area partly constitutes the area of the extension of the barrier layer and the area outside the core's edges, which adjoin around the extension of the core.

3. The absorbent article according to claim 1, wherein the covering layer is formed of an elastic nonwoven.

4. The absorbent article according to claim 1, wherein the covering layer is formed of an elastic laminate consisting of at least one layer and a textile-like layer.

5. The absorbent article according to claim 1, wherein the covering layer is formed of two layers with a plurality of intermediate elastic elements.

6. The absorbent article according to claim 1, the core comprises a surface layer facing towards the wearer.

7. The absorbent article according to claim 6, wherein the surface layer corresponds to the extension of the barrier layer.

8. The absorbent article according to claim 7, wherein the surface layer and the barrier layer are connected to one another, for example, by gluing, sewing, or welding using heat or ultrasound.

9. The absorbent article according to claim 1, wherein the pant part has a base colour that is selected from white, black, red, blue, violet, orange, yellow, green or indigo, as well as any other hue or mix thereof.

10. The absorbent article according to claim 1, wherein the pant part has a graphic pattern.

11. A packaging containing a plurality of absorbent articles, wherein at least one of the plurality of absorbent articles is the absorbent article according to claim 1, wherein the packaging has a code for skin tone.

12. The packaging according to claim 11, wherein the code is formed of a colour shade, which corresponds to the colour of the reference skin tone, a colour scale in colour in which the reference skin tone is depicted together with the surrounding skin tones, or it is stated in words which skin tone the article is designed for: for example, a Light skin tone, Yellow/Red skin tone or Dark skin tone, or a drawn figure in the shape of a person having the intended skin tone that the article is intended to match.

* * * * *